(12) United States Patent
Savona et al.

(10) Patent No.: US 8,567,395 B2
(45) Date of Patent: Oct. 29, 2013

(54) INHALER DEVICE FOR ADMINISTERING MEDICAMENTS THROUGH THE RESPIRATORY TRACTS

(76) Inventors: Antonio Savona, Cassano Magnago (IT); Fabrizio Cattaneo, Gavirate (IT)

( * ) Notice: Subject to any disclaimer, the term of this patent is extended or adjusted under 35 U.S.C. 154(b) by 1064 days.

(21) Appl. No.: 12/217,429

(22) Filed: Jul. 3, 2008

(65) Prior Publication Data

US 2009/0007910 A1 Jan. 8, 2009

(30) Foreign Application Priority Data

Jul. 6, 2007 (IT) .................................. MI07A1347

(51) Int. Cl.
*A61M 16/10* (2006.01)
(52) U.S. Cl.
USPC ............. 128/203.26; 128/203.12; 128/203.29
(58) Field of Classification Search
USPC ............. 128/202.26, 203.12, 203.17, 203.26, 128/203.27, 204.17, 203.19, 128/204.11–204.12, 206.13, 206.17, 206.19
See application file for complete search history.

(56) References Cited

U.S. PATENT DOCUMENTS

| | | | | |
|---|---|---|---|---|
| 670,084 A * | 3/1901 | Sloane | ...................... | 128/203.26 |
| 792,227 A * | 6/1905 | Merryman | ............... | 128/203.19 |
| 1,514,682 A * | 11/1924 | Wilson | ...................... | 128/203.27 |
| 2,005,229 A * | 6/1935 | Loos et al. | ............... | 128/203.27 |
| 2,077,437 A * | 4/1937 | Robinson | ................. | 128/203.26 |
| 2,591,992 A * | 4/1952 | Aerick | ....................... | 128/203.27 |
| 2,761,055 A * | 8/1956 | Ike | ................. | 392/393 |
| 2,894,508 A * | 7/1959 | Miles et al. | ............... | 128/206.17 |
| 3,080,624 A * | 3/1963 | Weber, III | ..................... | 422/125 |
| 3,152,240 A * | 10/1964 | Scott | ............................. | 392/403 |
| 3,526,226 A * | 9/1970 | Stern | ........................ | 128/203.27 |
| 3,938,512 A * | 2/1976 | Mausteller et al. | ...... | 128/202.26 |
| 4,597,917 A * | 7/1986 | Lunsford | ...................... | 261/153 |
| 4,677,976 A * | 7/1987 | Fujinuma et al. | ........ | 128/201.25 |
| 5,148,801 A * | 9/1992 | Douwens et al. | ........ | 128/203.16 |
| 5,524,616 A * | 6/1996 | Smith et al. | ............. | 128/205.27 |
| 5,538,013 A * | 7/1996 | Brannon | ....................... | 128/857 |
| 6,918,389 B2 * | 7/2005 | Seakins et al. | ........... | 128/203.27 |
| 2001/0042546 A1 * | 11/2001 | Umeda et al. | ............. | 128/206.21 |
| 2002/0117175 A1 * | 8/2002 | Kottayil et al. | ........... | 128/203.15 |
| 2005/0145250 A1 * | 7/2005 | Miyazawa et al. | ....... | 128/205.25 |
| 2006/0289004 A1 * | 12/2006 | Saez et al. | ................ | 128/201.24 |

OTHER PUBLICATIONS

Merriam-Webster definition of "recess", accessed at Merriam-Webster.com on Jan. 13, 2012.*

* cited by examiner

*Primary Examiner* — Lynne Anderson
*Assistant Examiner* — Kathryn E Ditmer
(74) *Attorney, Agent, or Firm* — Hedman & Costigan, P.C.; James V. Costigan; Kathleen A. Costigan

(57) ABSTRACT

An inhaler device for administering medicaments through the respiratory tracts comprises a disposable or single-use assembly including a heat source which can be actuated by a user for vaporizing a liquid medicament held near the heat source.

5 Claims, 2 Drawing Sheets

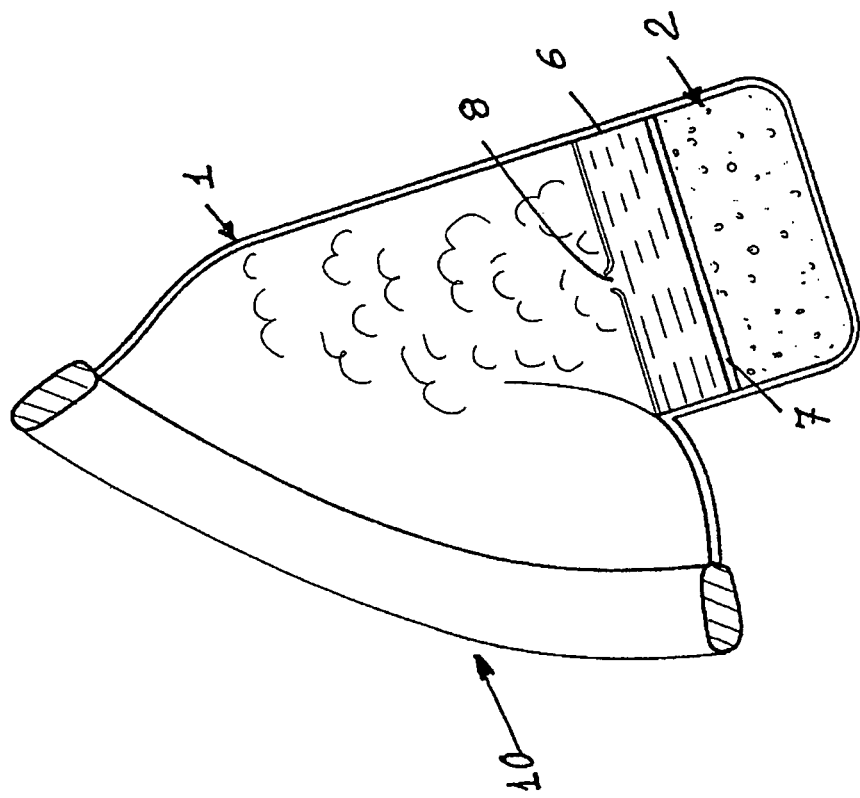
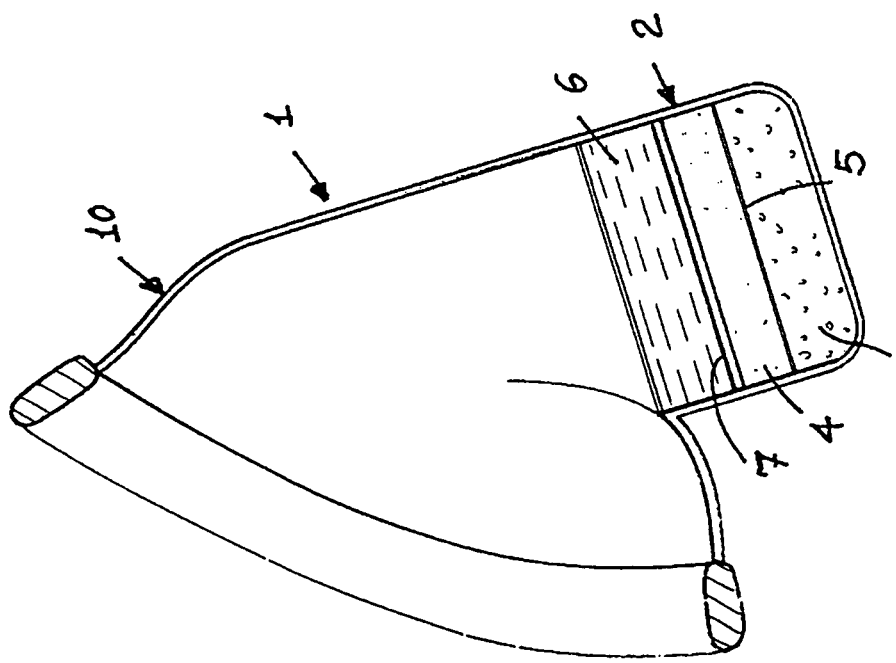

INHALER DEVICE FOR ADMINISTERING MEDICAMENTS THROUGH THE RESPIRATORY TRACTS

BACKGROUND OF THE INVENTION

The present invention relates to an inhaler device for administering medicaments in general through the respiratory tracts.

Prior inhaler devices for inhaling medicaments in general through the respiratory tracts of a user usually comprise a delivery assembly which is coupled to a small mask or a mouth-piece, provided for association with a user or patient.

The above inhaler devices, which are typically used in a home environment, require that, after use, the mask and mouth-piece be accurately cleaned, for preventing any bacterial growth which would represent a serious danger for a subsequent use of the inhaler device.

SUMMARY OF THE INVENTION

Accordingly, the aim of the invention is to overcome the above mentioned problem, by providing an inhaler device for administering medicaments in general through the respiratory tracts, which is so designed as to satisfy stringent hygienic requirements, while preventing bacterial flora or other polluting elements from proliferating.

Within the scope of the above mentioned aim, a main object of the invention is to provide such an inhaler device which can be used in a very simple and easy manner, and which, moreover, has a very reduced size and does not require, for a proper use thereof, any connections to electric power sources.

Yet another object of the present invention is to provide such an inhaler device which, owing to its specifically designed constructional features, is very reliable and safe in operation.

Yet another object of the present invention is to provide such an inhaler device which can be easily made and which, moreover, is very competitive from a mere economic standpoint.

According to one aspect of the present invention, the above mentioned aim and objects, as well as yet other objects, which will become more apparent hereinafter, are achieved by an inhaler device for administering medicaments in general through respiratory tracts, characterized in that said inhaler device comprises a disposable assembly including a heat source which can be actuated by a user for vaporizing a medicament liquid held near said heat source.

BRIEF DESCRIPTION OF THE DRAWINGS

Further characteristics and advantages of the present invention will become more apparent hereinafter from the following detailed disclosure of a preferred, though not exclusive, embodiment of an inhaler device for administering medicaments in general through respiratory tracts, which is illustrated, by way of an indicative, but not limitative, example in the accompanying drawings, where:

FIG. 2 is a cross-sectional view showing the inhaler device according to the invention before use; and FIG. 3 is a further cross-sectional view of the inventive inhaler device in a use condition.

DESCRIPTION OF THE PREFERRED EMBODIMENT

Figure 1:
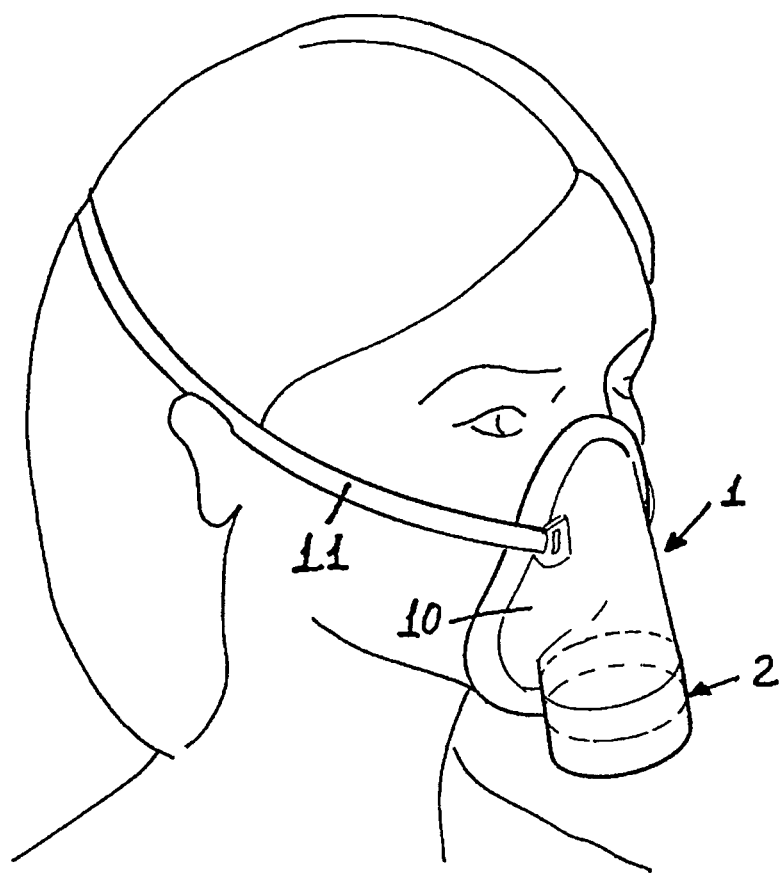
FIG. 1 is a schematic view showing the inhaler device according to the invention applied to a user or patient.

With reference to the number references of the above mentioned figures, the inhaler device for administering medicaments in general through the respiratory tracts of a user or patient, according to the present invention, which has been generally indicated by the reference number 1, comprises a disposable or single-use assembly, so designed as to be used, without the need of being coupled to power sources, and which, after having been used, can be disposed of, thereby solving all the problems related to a sterilizing of the device.

According to a preferred, though not exclusive, embodiment of the invention, the inhaler device 1 comprises a heat source, generally indicated by the reference number 2, which is advantageously made of a compartment 3, or recess, including calcium chloride and a compartment or recess 4 including water, said compartments being joined by a tearable membrane 5.

Thus, the mixing of water and calcium chloride will provide an exothermal reaction, causing a medicament product held in a medicament product vessel 6, which is separated by a bottom element 7 from the heat source, to be properly heated.

In this connection, it should be apparent that any suitable substance, adapted to provide an exothermal reaction, could be herein used.

The vessel 6 comprises an openable vessel mouth 8, therefrom the medicament product is ejected to be vaporized at the use time.

To the vessel 6 a respiratory mask 10, including a conventional resilient string element 11 for holding said mask at any desired position, is coupled.

In this connection it should be pointed out that the mask 10 and vessel 6 can be made as a single piece.

Optionally, the delivery mouth 8 can be coupled to a mouth piece or other like element allowing to provide an easy respiratory inhalation of the medicament product being vaporized.

Thus, the above disclosed construction provides an inhaler device which, for operation, must not be coupled to an electric power source and which, moreover, always provides a sterile element, since it will be disposed of after use.

From the above disclosure, it should be apparent that the invention fully achieves the intended aim and objects.

More specifically, the invention has provided a single-use facial respiratory mask inhaler device for covering a nose and a mouth of a user, for administering medicaments through respiratory tracts of said user, wherein said inhaler device comprises a facial mask to be coupled by a resilient string to a face of said user and including, extending from and under a chin of said user, an exothermal reaction heat source, said exothermal reaction heat source consisting of a bottom compartment of said mask containing calcium chloride and a top compartment of said mask containing water, said bottom and top compartments being separated by a tearable membrane, said facial mask further including, on a top of said water containing compartment, a vessel containing a medicament product to be evaporated by said exothermal reaction beat source at a use time of said mask, said medicament product vessel being separated by a bottom element from said heat source.

In practicing the invention, the used materials, as well as the contingent size and shapes, can be any, depending on requirements.

The invention claimed is:

1. A single-use facial respiratory mask inhaler device for covering a nose and a mouth of a user, for administering a medicament liquid through respiratory tracts of said user, wherein said inhaler device comprises a facial mask to be coupled by a resilient string to a face of said user and including, extending from and under a chin of said user, an exothermal reaction heat source, said exothermal reaction heat source being integral with said mask and consisting of a bottom compartment of said mask containing a substance adapted to provide an exothermal reaction as said substance comes into contact with water and a top compartment of said mask containing water, said bottom and top compartments being separated by a tearable membrane, said facial mask further including, on a top of said water containing compartment, a vessel containing a medicament product to be evaporated by said exothermal reaction heat source at a use time of said mask, said medicament product vessel being separated by a bottom element thereof.

2. An inhaler device according to claim 1, wherein said substance consists of calcium chloride.

3. An inhaler device according to claim 1, wherein said medicament product vessel is made in a single piece with said facial mask.

4. An inhaler device according to claim 1, wherein said medicament product vessel comprises an openable mouth for ejecting said evaporated medicament product therefrom.

5. An inhaler device according to claim 4, wherein said delivering mouth can be coupled to a mouth piece to facilitate a respiratory inhalation of said medicament liquid being vaporized.

* * * * *